(12) United States Patent
Henschke et al.

(10) Patent No.: US 7,873,196 B2
(45) Date of Patent: Jan. 18, 2011

(54) MEDICAL IMAGING VISIBILITY INDEX SYSTEM AND METHOD FOR CANCER LESIONS

(75) Inventors: Claudia Ingrid Henschke, New York, NY (US); David F. Yankelevitz, Brooklyn, NY (US); Anthony P. Reeves, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 952 days.

(21) Appl. No.: 11/688,980

(22) Filed: Mar. 21, 2007

(65) Prior Publication Data

US 2007/0223807 A1 Sep. 27, 2007

Related U.S. Application Data

(60) Provisional application No. 60/784,683, filed on Mar. 22, 2006.

(51) Int. Cl.
*G06K 9/00* (2006.01)
(52) U.S. Cl. .................................. 382/128
(58) Field of Classification Search ............ 382/128, 382/131, 159, 160, 224, 225
See application file for complete search history.

(56) References Cited

U.S. PATENT DOCUMENTS

| | | | |
|---|---|---|---|
| 5,311,131 A | 5/1994 | Smith | |
| 5,815,591 A | 9/1998 | Roehrig et al. | |
| 5,917,929 A | 6/1999 | Marshall et al. | |
| 6,014,452 A | 1/2000 | Zhang et al. | |
| 6,035,056 A | 3/2000 | Karssemeijer | |
| 6,075,879 A | 6/2000 | Roehrig et al. | |
| 6,143,512 A * | 11/2000 | Markovic et al. | 435/21 |
| 6,198,838 B1 | 3/2001 | Roehrig et al. | |
| 6,238,342 B1 | 5/2001 | Feleppa et al. | |
| 6,243,486 B1 | 6/2001 | Weiss | |
| 6,263,092 B1 | 7/2001 | Roehrig et al. | |
| 6,301,378 B1 | 10/2001 | Karssemeijer et al. | |
| 6,404,908 B1 | 6/2002 | Schneider et al. | |
| 6,580,818 B2 | 6/2003 | Karssemeijer et al. | |
| 6,640,001 B2 | 10/2003 | Roehrig et al. | |
| 6,724,917 B1 * | 4/2004 | Ohashi et al. | 382/104 |
| 6,738,499 B1 * | 5/2004 | Doi et al. | 382/128 |
| 6,766,043 B2 | 7/2004 | Zeng | |
| 6,909,794 B2 | 6/2005 | Caspi | |
| 6,909,795 B2 | 6/2005 | Tecotzky et al. | |
| 6,909,797 B2 | 6/2005 | Romsdahl et al. | |
| 6,925,200 B2 | 8/2005 | Wood et al. | |
| 7,054,473 B1 | 5/2006 | Roehrig et al. | |
| 7,583,827 B2 * | 9/2009 | Hansen et al. | 382/128 |

(Continued)

OTHER PUBLICATIONS

R2 Technology, Inc., What is CAD?, 2004.

(Continued)

*Primary Examiner*—Bhavesh M Mehta
*Assistant Examiner*—Shervin Nakhjavan
(74) *Attorney, Agent, or Firm*—Citadel Patent Law; George A. Leone (57) ABSTRACT

A visibility index for medical images. The method includes generating a visibility index from a training set of images; making a number of measurements of a set of features from an image of an abnormality that is not a member of the training set; and combining the number of measurements to generate a visibility score mapped to the visibility index.

16 Claims, 7 Drawing Sheets

U.S. PATENT DOCUMENTS

| | | | |
|---|---|---|---|
| 2002/0159622 A1 | 10/2002 | Schneider | |
| 2002/0181739 A1* | 12/2002 | Hallowell et al. | 382/100 |
| 2003/0016850 A1 | 1/2003 | Kaufman | |
| 2003/0095696 A1 | 5/2003 | Reeves | |
| 2004/0184647 A1 | 9/2004 | Reeves | |
| 2004/0252870 A1 | 12/2004 | Reeves | |
| 2005/0013471 A1 | 1/2005 | Snoeren et al. | |
| 2005/0163360 A1 | 7/2005 | Snoeren et al. | |
| 2005/0201624 A1* | 9/2005 | Hara et al. | 382/232 |
| 2006/0018524 A1* | 1/2006 | Suzuki et al. | 382/128 |
| 2006/0147099 A1 | 7/2006 | Marshall | |
| 2006/0239544 A1 | 10/2006 | Yankelevitz | |
| 2007/0025624 A1* | 2/2007 | Baumberg | 382/232 |
| 2009/0080732 A1* | 3/2009 | Zhou et al. | 382/128 |
| 2010/0027838 A1* | 2/2010 | Mian et al. | 382/100 |

OTHER PUBLICATIONS

National Cancer Institute, Improving Methods for Breast Cancer Detection and Diagnosis, Apr. 26, 2002.

Ginneken, Computer-Aided Diagnosis in Chest Radiography: A Survey, IEEE Transactions on Medical Imaging, vol. 20, No. 12, Dec. 2001.

Swensen,MD et al., Scanlon Symposium—Lung Cancer, Mar. 12, 2000.

* cited by examiner

MEDICAL IMAGING VISIBILITY INDEX SYSTEM AND METHOD FOR CANCER LESIONS

RELATED APPLICATION

This application is related to co-pending provisional application of Yankelevitz, et al., application No. 60/784,683, filed Mar. 22, 2006, entitled "MEDICAL IMAGING VISIBILITY INDEX SYSTEM AND METHOD FOR CANCER LESIONS" and, by this reference, claims the benefit of the priority filing date of the co-pending provisional application. All of the contents of the aforementioned co-pending provisional application No. 60/784,683 are incorporated by reference.

FIELD OF THE INVENTION

The present invention relates generally to analysis of medical imaging data, and, more particularly to analysis of medical imaging data using a visibility index for cancer lesions.

BACKGROUND OF THE INVENTION

A primary reason for malpractice suits against radiologists is missed cancer. Such suits are often based on missed breast cancer on mammography and missed lung cancer on chest x-rays. To a smaller degree, errors on CT scans have also led to legal actions. Currently, there is no objective standard for measuring the effectiveness of human observers and/or computer controlled visioning equipment for finding cancer lesions. Missed cancers are often reviewed using hindsight and knowledge of facts not available to the original observer. As a result, such reviews often produce diametrically opposed opinions regarding whether an incidence of missed cancer fell below a standard of care.

In a typical scenario, a patient has undergone an imaging procedure producing a medical image. Although present in the medical image, a lesion is missed and not identified by a reader, such as a radiologist. Subsequently, cancer is discovered when the patient either has the imaging done again or has become symptomatic. A malpractice claim may result where it is typically alleged that the radiologist should have seen the lesion on the original study. It may be further alleged that, because the lesion was missed, it has progressed making the lesion less amenable to treatment and thereby increasing the risk of death.

One of the most challenging aspects of such malpractice cases turns on whether the missed abnormality was readily identifiable on the initial examination according to accepted medical practice. Unfortunately, criteria for determining the visibility of a cancerous abnormality are quite vague. A lesion may have low conspicuity on an early scan image. However, once a lesion is known to exist in a specific location, an informed observer may opine that the lesion is fairly obvious on a medical image. Using such hindsight, a fact-finding body, such as a jury, may make a determination of malpractice in questionable circumstances. As a general rule, when an expert participates in a case, the expert reviews the images and determines whether a particular lesion should have been missed or found. Often the expert reviews a series of images taken over time and determines the point at which the lesion should have been visible. Ultimately, there are no objective standards for determining the visibility of lesions on medical images.

A visibility index for medical imaging has heretofore been lacking. As a result no objective standard for measuring the effectiveness of the interpretation of a medical image, whether by human or automated system, has been made available.

SUMMARY OF THE INVENTION

In one example, a system and method for creating and using a visibility index for medical images is described. The method includes generating a visibility index from a training set of images;

making a number of measurements of a set of features from an image of an abnormality that is not a member of the training set; and combining the number of measurements to generate a visibility score mapped to the visibility index.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DESCRIPTION OF THE PREFERRED EMBODIMENTS

Preliminarily, it should be noted that while a particular system and method described in detail herein is for analyzing medical imaging data, such as radiology data, this is not by way of limitation, but solely for the purposes of illustration, and the system and method described may be employed for analyzing data of other types.

Figure 1:
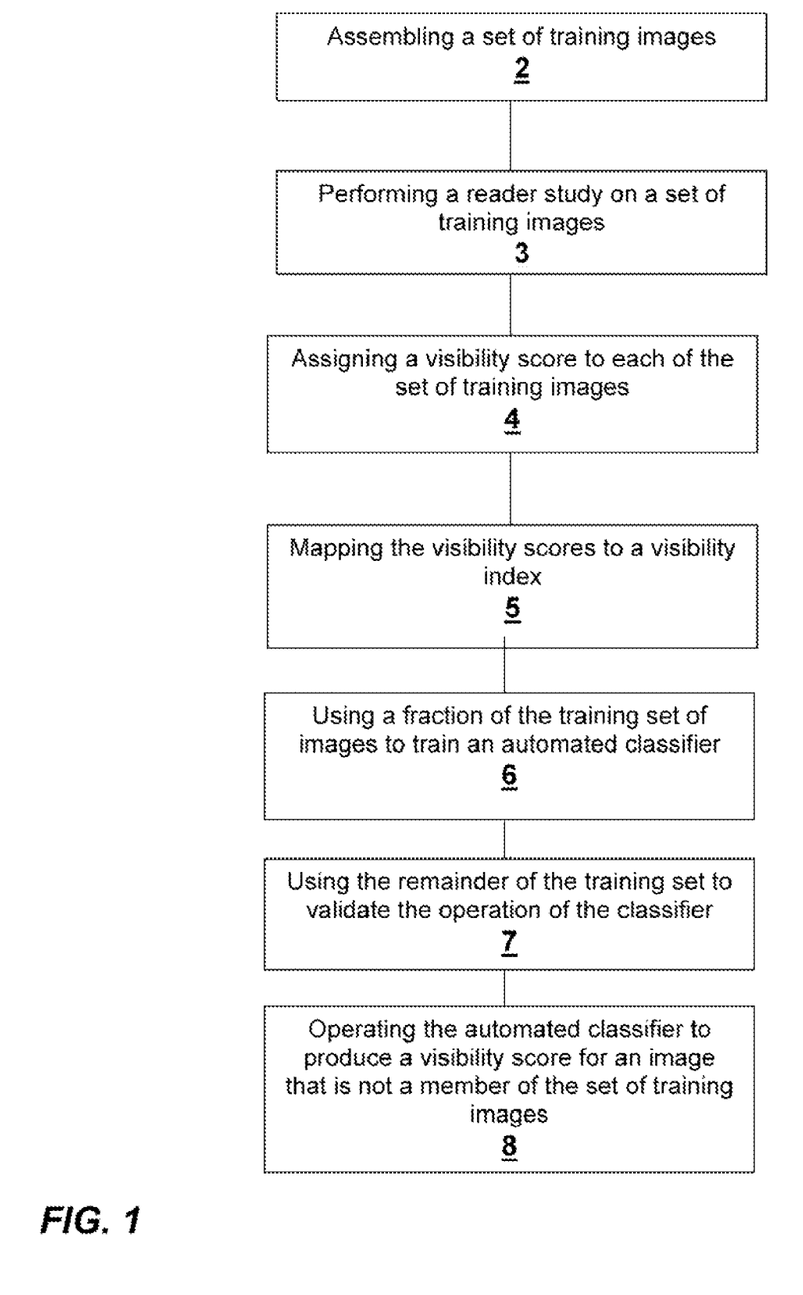
FIG. 1 is a schematic view of a process flow chart for generating and using a visibility index for medical images.

Referring now to FIG. 1, a schematic view of a process flow chart for generating and using a visibility index for medical images is shown. At step 2 a set of training images is assembled. The set of training images may advantageously comprise medical images exhibiting, for examples lesions in a chest CT scan that have been previously identified and confirmed as cancer. At step 3 a reader study is performed by a panel of experts on the set of training images. At step 4 the reader panel assigns a visibility score to each member of the set of training images. At step 5 the visibility scores are mapped to a visibility index as visibility index scores. At step 6 a fraction of the set of training images is used to train an automated classifier to automatically generate visibility scores for images. Each of the fractional set of images is tagged with its assigned visibility index score, at step 7 the remainder of the training set to is used to validate the operation of the automated classifier. At step 8 the trained automated classifier is operated to produce at least one visibility score for at least one image, where the visibility score is normalized to the visibility index.

Figure 2:
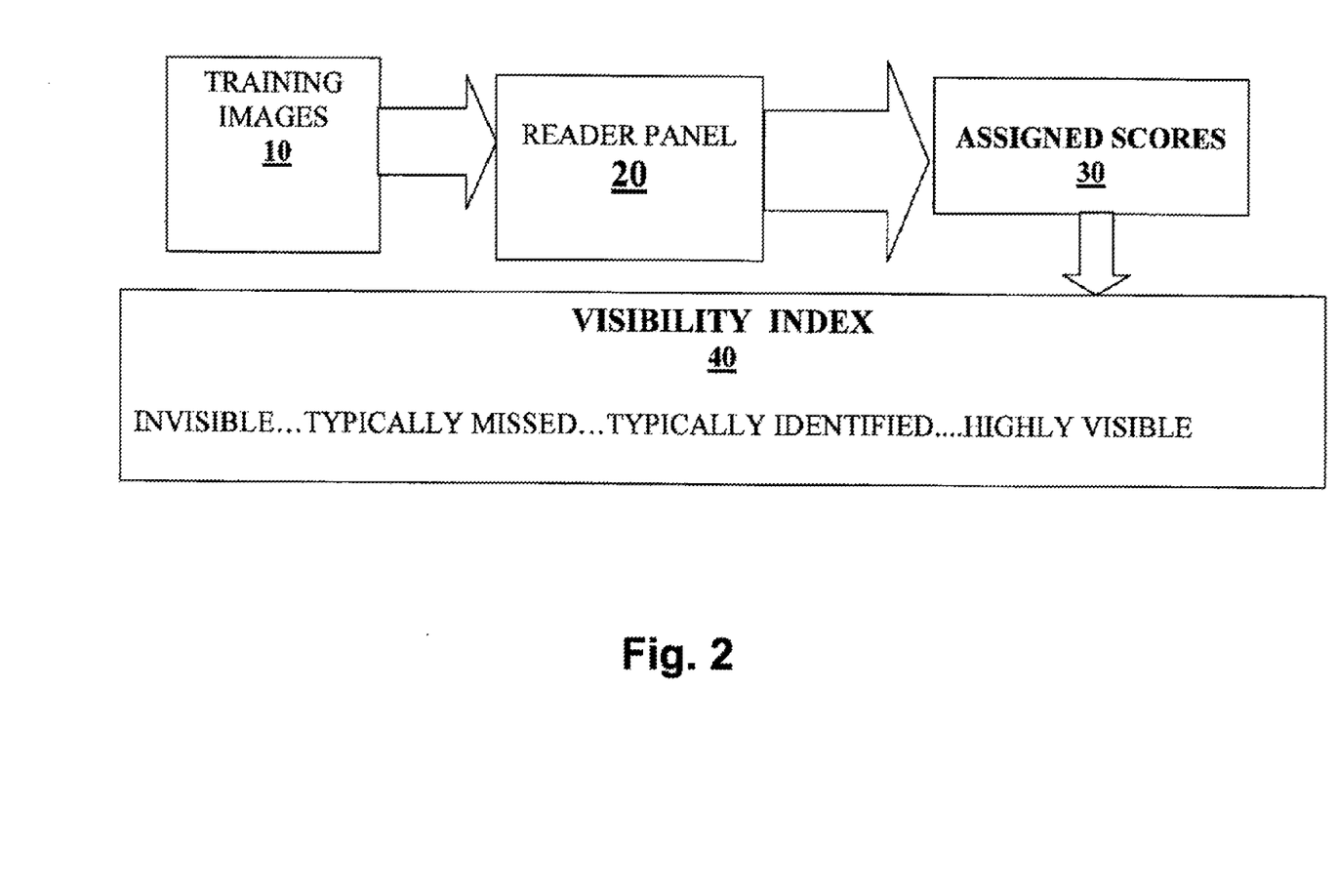
FIG. 2 is a schematic view of system architecture for generating a visibility index for medical images.

Referring now to FIG. 2, a schematic view of system architecture used in an example method for generating a visibility index for medical images is shown. A set of training images 10 of known conditions is provided to a reader panel of professionals 20. The reader panel 20 assigns visibility scores 30 to each of the known conditions ranging from invisibility to highly visible conditions. The visibility scores 30 are then mapped into a visibility index 40. The visibility index 40 preferably includes sub-ranges corresponding to typical radiologist performance so as to determine whether a particular abnormality on a particular study was reasonably missed. The sub-ranges are mapped to visibility scores and may include, for example, "invisible," "typically missed," "typically identified," "highly visible," and other designations.

Each of the visibility scores 30 is also assigned to its respective medical image and later used as one of a set of target output scores for training an automated classifier using at least a portion of the set of training images 10 as described below with reference to FIG. 3.

The medical imaging data may include portions of medical scans and/or entire scans. The set of training images 10 of known conditions may include, for example, radiology data, radiology images, medical image data, pathology image data, digital images of medical data, photographic images, scanned images molecular imaging data and medical genetic imaging data. The medical imaging data may be generated from medical imaging procedures, including, for examples Computerized Tomography (CT) scans, Magnetic Resonance Imaging (MRI), Positron Emission Technology (PET), X-Rays, Vascular Interventional and Angiogram/Angiography procedures, Ultrasound imaging, and similar procedures. A set of training images preferably comprises images of like disease conditions from the same type of medical imaging device. However, the process of the invention is not so limited and there may be applications wherein training sets of dissimilar images may prove useful.

In other cases, simulated nodules and/or synthetically generated images may be used for training, validating or other purposes. In one example, synthetic or actual images may be employed to rate an imaging system or a computer aided diagnostic device using the visibility index. In another example, the visibility index may be employed for grading a database of nodule images.

Figure 3:
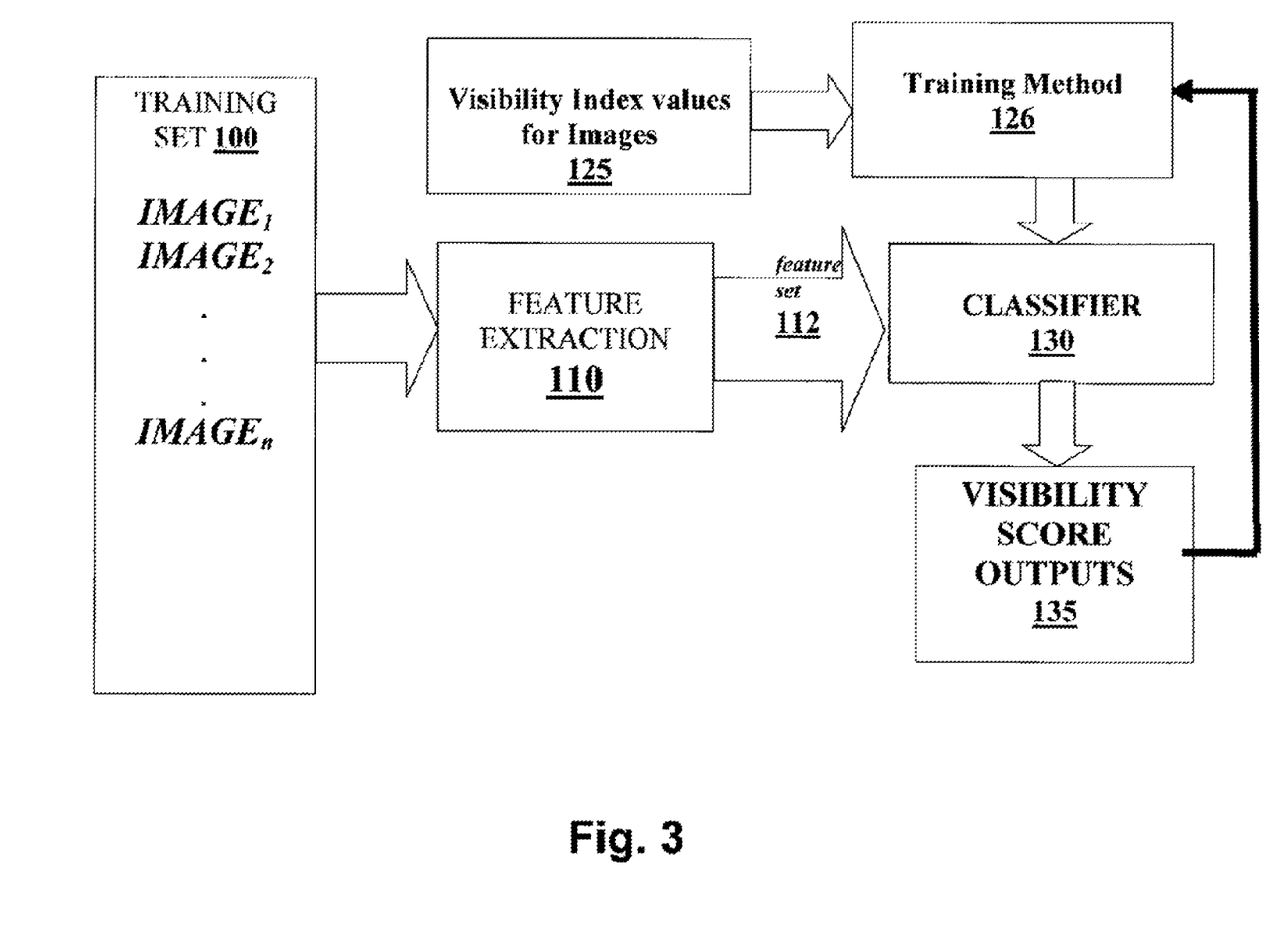
FIG. 3 schematically shows a process for building a classifier using visibility scores and image features.

Referring now to FIG. 3, training process architecture for training a classifier using visibility scores and image features is schematically shown. A fraction 100 of the set of training images comprising a plurality of images, IMAGE1, IMAGE2 . . . IMAGEn, are introduced into a feature extraction algorithm processor 110. The feature extraction processor 110 generates a plurality of feature for each of the set of training images and transmits the plurality of features 112 for each of the set of training images and transmits the features to the automated classifier 130. The automated classifier 130 output is preferably a visibility score output, which is preferably a number that may be mapped into the visibility index. During supervised classifier training the visibility index output is transmitted to a training method 126 where it is compared with known visibility index values 125.

In one exemplary embodiment, the classifier 130 may comprise a neural network. Neural networks are characterized by having processing units{uj}, where each uj has a certain activation level aj(t) at any point in time. Weighted interconnections between the various processing units determine how the activation of one unit leads to input for another unit. An activation rule acts on the set of input signals at a unit to produce a new output signal, or activation. A learning rule that specifies how to adjust the weights for a given input/output pair may also be optionally included.

In other exemplary embodiments, the classifier 130 may advantageously employ conventional techniques such as linear regression algorithms, nearest neighbor thresholds, discriminant analysis, Bayesian approaches, adaptive pattern recognition, fuzzy-set theory, and adaptive processing, as well as artificial neural networks, Kohonen maps and equivalents. For a list of features and classifiers previously used to classify nodule candidates for computer-aided diagnosis see van Ginneken, et al.) "Computer-Aided Diagnosis in Chest Radiography: A Survey," IEEE Transactions on Medical Imaging Vol. 20, No. 12, pp. 1228-1237, 2001.

Figure 7:
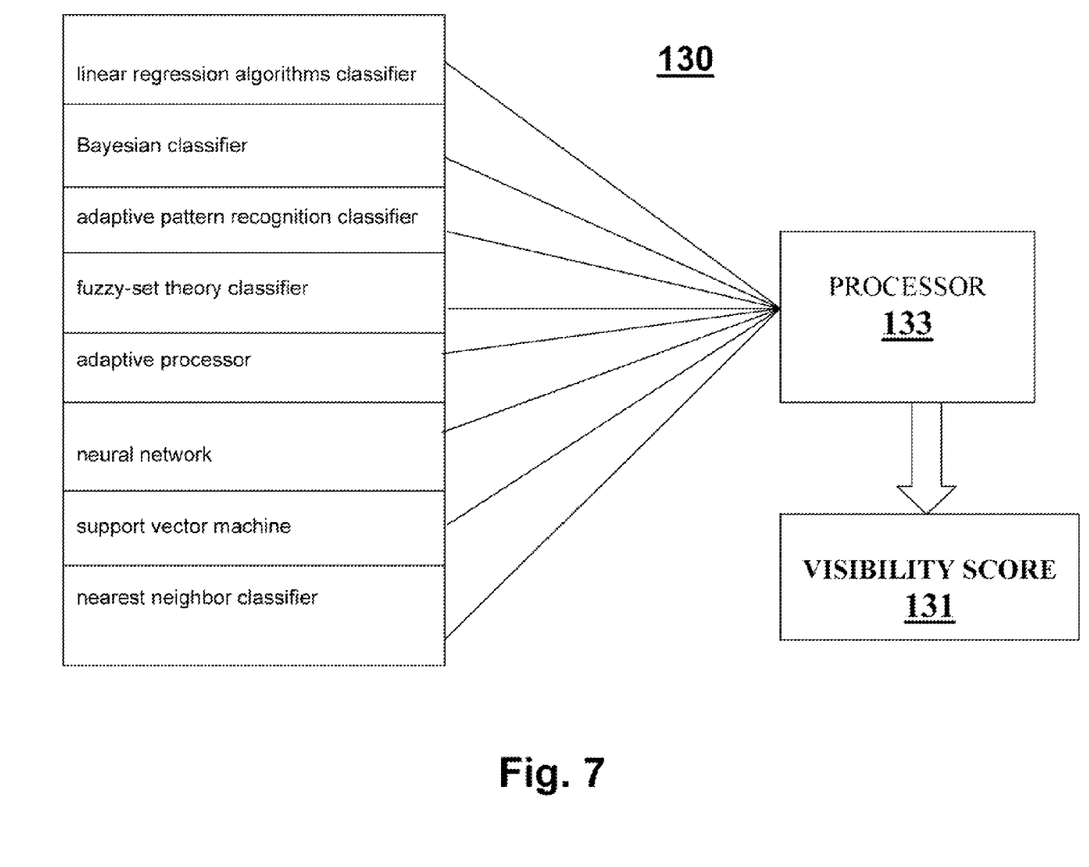
FIG. 7 schematically shows an exemplary embodiment of a classifier using visibility scores and image features.

Referring now to FIG. 7, an exemplary embodiment of a classifier using visibility scores and image features is schematically shown. The classifier 130 may advantageously comprise one or more sub-classifiers including a linear regression algorithms classifier, a Bayesian classifier, an adaptive pattern recognition classifier, a fuzzy-set theory classifier, an adaptive processor, a neural network, a support vector machine, a nearest neighbor classifier and the like. A plurality of classifiers may be used in parallel, in series or in other combinations to produce a visibility score 131 based on the visibility index. In one exemplary embodiment as shown, output results from each of the plurality of classifiers may be processed together in a processor 133 to produce an overall or average visibility score. Many such schemes are known in the art, as are training methods.

Examples of useful features for classifying nodule candidates from chest radiography images include radius, contrast, distance from hilum, shape features, features based on histograms and filter outputs applied to regions of interest (ROIs), location, degree of circularity, degree of irregularity, density, texture, power spectrum features, diameter, size, gradient measures, statistical parameters including mean, maximum, width, and standard deviation, combinations of such features and the like. The features may also be image quality automatically assigned values based on grey-scale, color, size, border definition and other characteristics typically used in image processing. In one exemplary embodiment, the feature extraction processor, classifier, error processor and parameter correction processor may advantageously be operated as software programs residing in a computer, such as a personal computer or the like.

Figure 4:
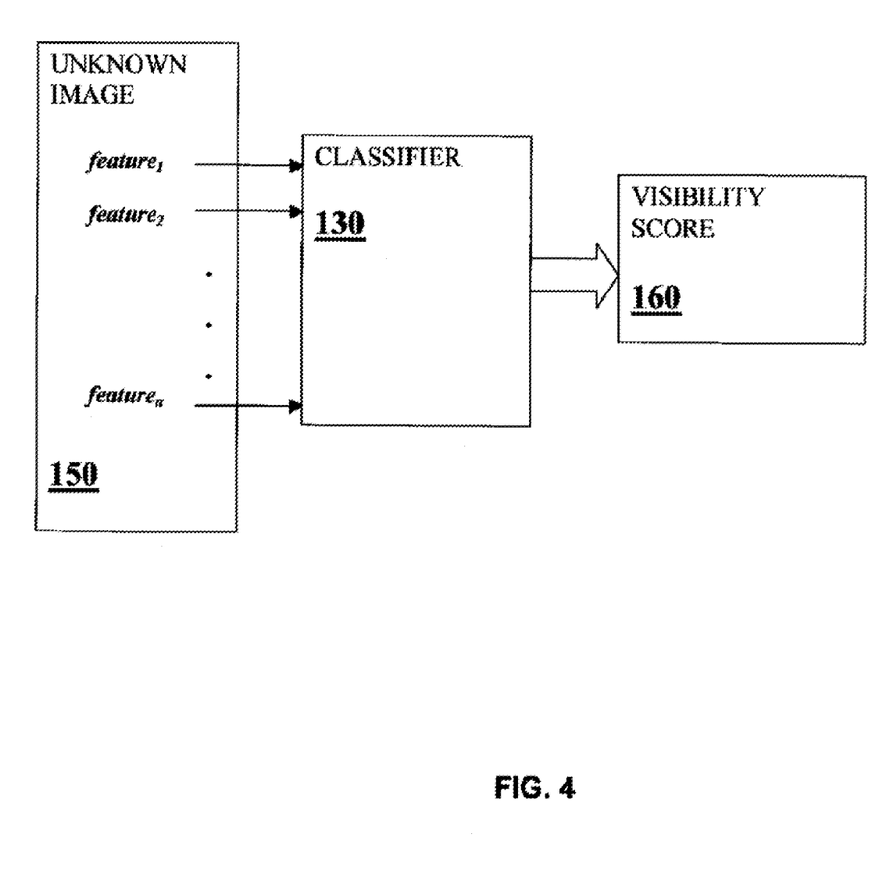
FIG. 4 schematically shows a process for using a classifier constructed with a visibility index.

Referring now particularly to FIG. 4, a process for using a classifier constructed with the visibility index of the invention is schematically shown. The now trained classifier 130 may be used to score or classify images that are not members of the training set, thus generating an objective score that can be read against the visibility index. A series of features 1 . . . n from unknown image 150 is introduced into classifier 130. The classifier 130 produces a visibility score 160. Since the classifier is based on the visibility index, the score can be used objectively to determine visibility of a medical condition.

Figure 5:
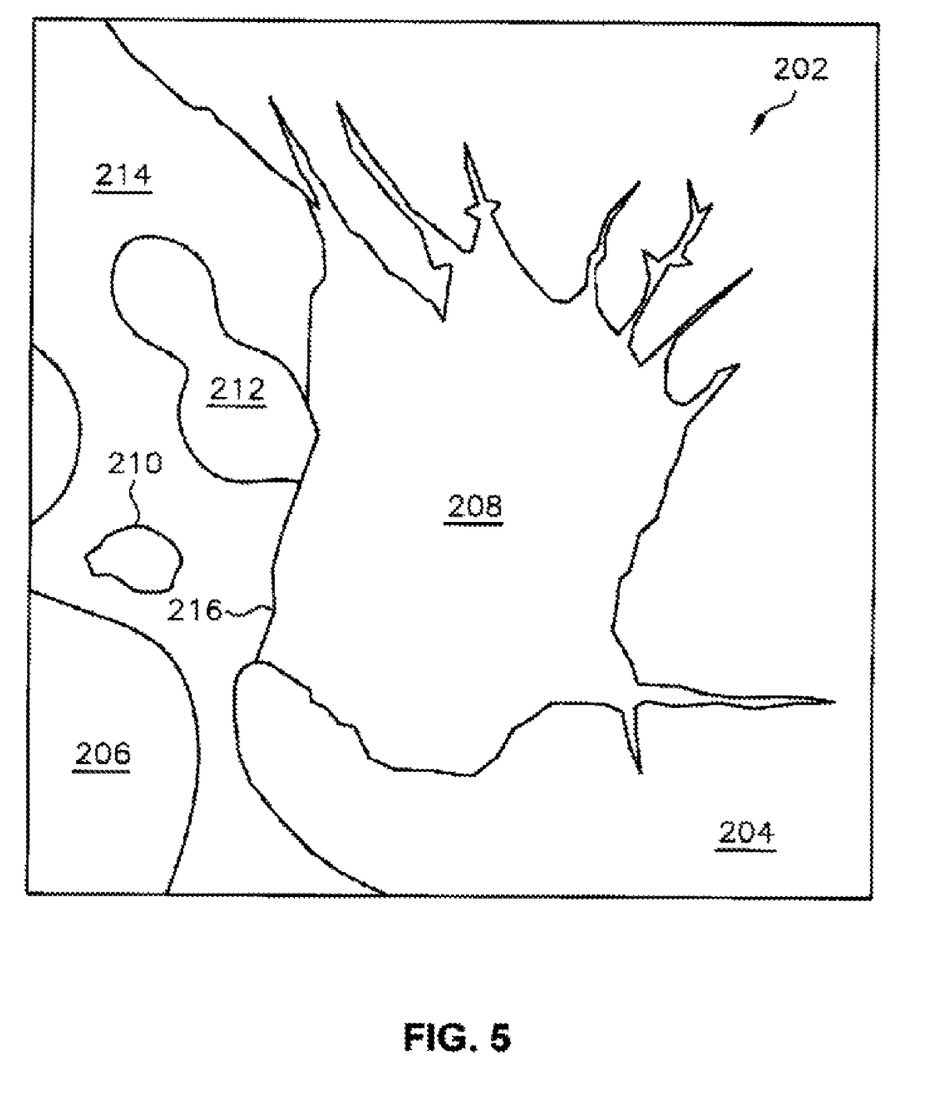
FIG. 5 schematically shows an exemplary medical image of a CT image of a large pulmonary nodule as may be presented for scoring by a visibility index.

Referring now to FIG. 5, an exemplary medical image of a CT image slice through a large pulmonary nodule as may be scored by the present invention is shown. A CT image 214 shows a pulmonary nodule 202 comprising a mass substantially bounded within region 208 within lung portion 204. Other body features include a spinal portion 206 and other features 210 and 212 adjacent the lung. The pulmonary nodule 202 typically will include spicules that emanate from the nodule. Exemplary features extracted from such a pulmonary nodule may advantageously comprise a plurality of physical parameters including size, density, sharpness of the nodule's border, number of vessels attached to the nodule and percentage of the border in contact with a lung, surrounding structures, and homogeneity of the nodule and combinations of these features.

Note that, in some cases a nodule may be present in an image being scored, but due to shadows, lighting or proximity to other organs, may be particularly difficult to discern. Since the location of the nodule is known, a radiologist may employ available computer drawing tools to outline the nodule, using, for example, boundary 216, before it is scored by the classifier in order to ensure a better result. One example of such useful computer drawing tools include those described in U.S. patent application Ser. No. 11/552,516 to Yankelevitz et al., filed Oct. 24, 2006 and entitled, "MEDICAL IMAGING SYSTEM FOR ACCURATE MEASUREMENT EVALUATION OF CHANGES IN A TARGET LESION," the full disclosure and contents of which are incorporated herein by reference.

Figure 6:
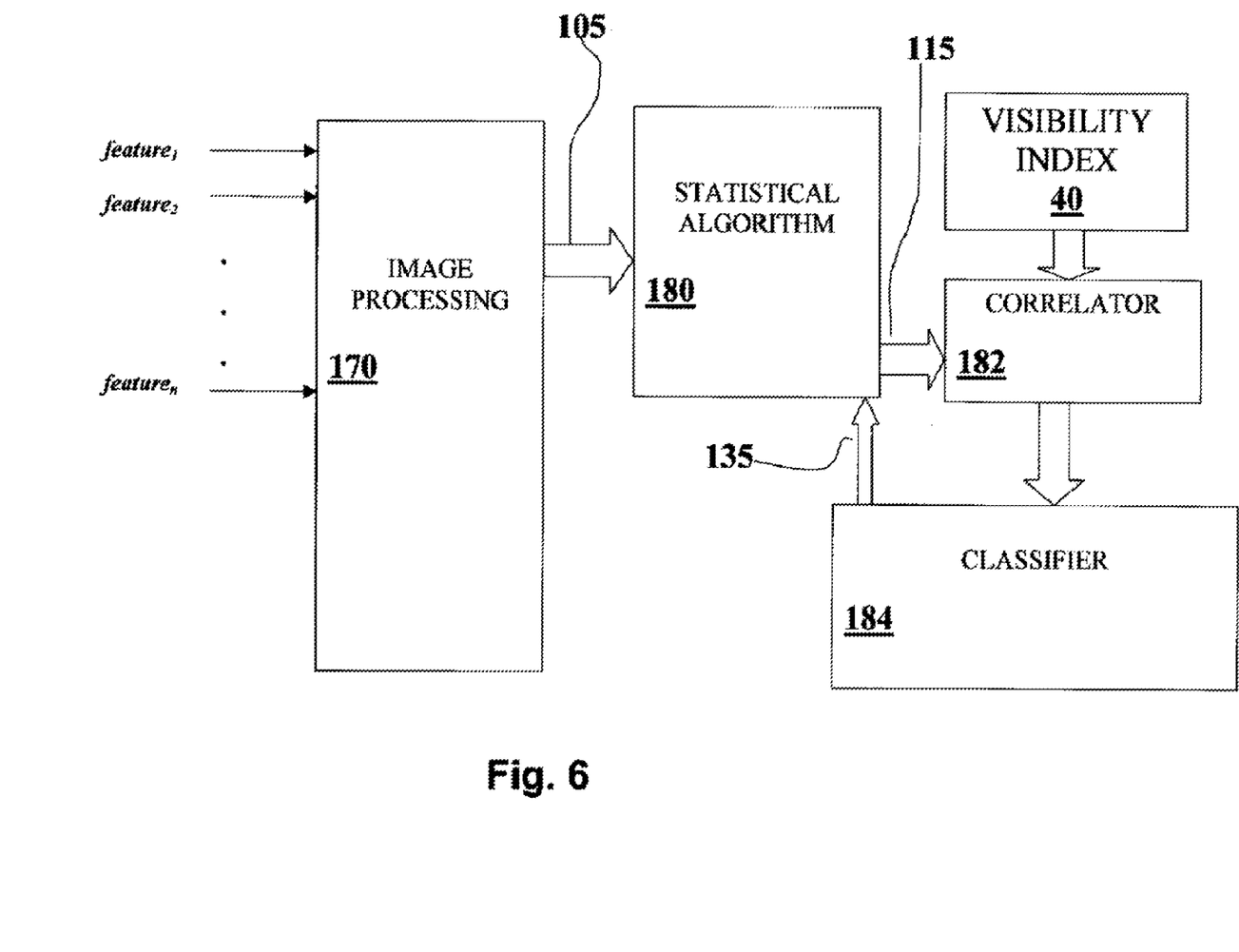
FIG. 6 schematically shows an alternative process for building a classifier using visibility scores and image features.

Referring now to FIG. 6, an alternative process for building a classifier using visibility scores and image features is schematically shown. A plurality of features 1, 2 . . . , n of each of a set of training images is processed in an image processor 170 for image qualities to generate processed data 105. The features may be assigned image quality values automatically based on grey-scale, color, size, border definition and other characteristics typically used in image processing. The processed data 105 is provided to a statistical algorithm processor 180 for statistical analysis. The statistical algorithm processor 180 may advantageously be operated as a software program contained in a computer, such as a personal computer. The statistical algorithm processor 180 may advantageously employ statistical techniques such as linear regression algorithms, Bayesian approaches, adaptive pattern recognition, fuzzy-set theory, and may also include adaptive processing, neural networks and the like. The images and selected features are correlated in correlator 182 to the visibility index 40 using the analysis results 115 to build a scoring algorithm or classifier 184.

For lung nodules a classifier may be constructed using images representing a plurality of varying categories of nodules as inputs for training and reader studies. Further, the varying categories of nodules may advantageously comprise actual cases or computer generated nodule images. The visibility index may be generated from reader study tests where combinations of cases, with a range of findings, are presented to a group of radiologists for interpretation.

The reader study is not limited to human readers. The visibility index may also be applied to automated medical imaging systems in order to provide an indication of the quality and/or reliability of such medical imaging systems. For specific uses, a medical imaging system can be tested to measure its performance on nodules with pre-selected criteria.

While specific embodiments of the invention have been illustrated and described herein it is realized that numerous modifications and changes will occur to those skilled in the art. It is therefore to be understood that the appended claims are intended to cover all such modifications and changes as fall within the true spirit and scope of the invention.

What is claimed is:

1. A method for using a visibility index for medical images, the method comprising:

performing a plurality of reader studies on a set of training images to assign a training visibility score to each member of the set of training images, to build a set of training visibility scores;

operating a processor to map the set of training visibility scores to a visibility index so that the visibility index is derived from the plurality of reader studies, wherein the visibility index has a range including a portion corresponding to typical radiologist performance so as to allow an objective determination as to whether a particular abnormality on a particular image was reasonably missed by a reader;

operating a processor for making a number of measurements of a set of features from an image of a selected abnormality that is not a member of the training set; and operating a processor for combining the number of measurements and to generate an assigned visibility score mapped to the visibility index where the assigned visibility score's mapping to the visibility index determines whether the selected abnormality was reasonably missed by a reader.

2. The method of claim 1 wherein the visibility index comprises a graduated index ranging from highly visible to invisible.

3. The method of claim 1 wherein the step of measuring includes measuring a plurality of physical parameters of the abnormality image.

4. The method of claim 3 wherein the plurality of physical parameters comprises pulmonary nodule features including size, density, sharpness of the nodule's border, number of vessels attached to the nodule and percentage of the border in contact with a lung, surrounding structures, and homogeneity of the nodule.

5. The method of claim 1 wherein the plurality of reader studies are selected with a plurality of varying categories of nodules as inputs for testing.

6. The method of claim 5 wherein the plurality of varying categories of nodules comprise actual cases.

7. The method of claim 5 wherein the plurality of varying categories of nodules comprise computer generated nodule images.

8. The method of claim 1 wherein the visibility index comprises an index generated from reader study tests where a combination of cases, with a range of findings, are presented to a group of radiologists for interpretation.

9. The method of claim 8 wherein the reader study tests results are placed into an overall score.

10. The method of claim 9 wherein the overall score is generated from at least a selected one of a linear regression classifier, a Bayesian classifier, an adaptive pattern recognition classifier, a fuzzy-set theory classifier, an adaptive processor, a neural network, a support vector machine, and a nearest neighbor classifier.

11. The process of claim 1 further comprising using a fraction of the set of training images to train an automated classifier to automatically generate another set of visibility scores for images, where each image in the second set of training images is tagged with its assigned visibility index score.

12. The process of claim 11 further comprising using a remainder of the set of training images to validate the training of an automated classifier.

13. The process of claim 11 further including operating the trained automated classifier to produce at least one visibility score for at least one image, where the visibility score is mapped to the visibility index.

14. The process of claim 11 wherein the set of training images comprises a selected one of medical images, simulated images and computer generated images.

15. The process of claim 1 wherein the reader is a radiologist.

16. The process of claim 1 wherein the reader comprises an automated medical imaging system.

* * * * *